United States Patent [19]

Antranikian

[11] Patent Number: 5,569,599
[45] Date of Patent: Oct. 29, 1996

[54] KERAINASE FROM FERVIDOBACTERIUM PENNAVORANS DSM 7003

[75] Inventor: Garabed Antranikian, Seevetal, Germany

[73] Assignee: Degussa Aktiengesellschaft, Frankfurt, Germany

[21] Appl. No.: 290,762

[22] PCT Filed: Mar. 12, 1993

[86] PCT No.: PCT/EP93/00569

§ 371 Date: Nov. 2, 1994

§ 102(e) Date: Nov. 2, 1994

[87] PCT Pub. No.: WO93/18134

PCT Pub. Date: Sep. 16, 1993

[30] Foreign Application Priority Data

Mar. 13, 1992 [DE] Germany ............ 42 08 275.7

[51] Int. Cl.⁶ .................. C12N 9/52; C12N 1/12; C12P 21/06; C07G 17/00
[52] U.S. Cl. ............. 435/220; 435/68.1; 435/252.1; 435/267; 435/822
[58] Field of Search .............. 435/220, 252.1, 435/822, 68.1, 267

[56] References Cited

PUBLICATIONS

Takami et al., Appl. Microbiol. Biotechnol., 30: 120–124, 1989.
Takami et al., Biosci. Biotech. Biochem., 56(10), 1667–1669, 1992.

Primary Examiner—David M. Naff
Attorney, Agent, or Firm—Cushman Darby & Cushman

[57] ABSTRACT

An enzyme composition containing keratinase is obtained from *Fervidobacterium pennavorans* DSM 7003. The composition is capable of degrading keratin-containing substrates such as feathers, hair and horn within a few days at between 50° and 105° C. and at a pH of between 4 and 12 under anaerobic conditions. A pH of 10.5 and a temperature of 70° C. or greater are preferred. Dissolving of the substrate can be at least 50% by weight after 24 hours, and in 1 to 4 days the entire substrate can be dissolved. Pretreatment of the substrate at a temperature of 120° C. or greater is not required.

5 Claims, 4 Drawing Sheets

0d

1d

2d

KERAINASE FROM FERVIDOBACTERIUM PENNAVORANS DSM 7003

The invention is relative to a novel microorganism with proteolytic properties, an enzyme composition obtainable from the microorganism, the use of the microorganism as well as methods of hydrolysis especially of keratin.

DESCRIPTION OF THE STATE OF THE ART

It is known that special enzymes, the proteases, hydrolyse proteins, giving rise to oligopeptides and, finally, amino acids. These enzymes are also formed from microorganisms such as e.g. from bacteria of the genus Pseudomonas, Bacillus or Proteus. A few enzymes, the so-called thermophilic enzymes, exhibit the above-named activity even at temperatures $\geq 70°$ C., thus making possible hydrolyses which are of interest, especially to industry. E.g. thermophilic microorganisms are a source for such thermophilic enzymes. A survey of this is offered by BFE 9, No. 7/8, pp. 466–470 (1992) in the article "Thermophilic Enzymes as Industrial Catalysts?" by K. Peek et al. A further enzyme which still exhibits a certain activity above 70° C. is known from Biosci. Biotech. Biochem., 56 (10), pp. 1667–9 (1992). This enzyme also exhibits, in addition to usual proteolytic properties, a certain keratinase activity. Thus, hairs were attacked with this enzyme at a temperature up to 90° C.; however, this was at a pH of 11.0 and over a period of 1 h, although the enzyme had already lost one half of its activity after 10 min already under the conditions indicated (see Appl. Microbiol. Biotechnol. (1989) 30, pp. 120–124). Since the decomposition of human hair presented in Biosci. in FIG. 2b exhibits even at temperatures above 80° C. an even higher decomposition, this decomposition must be of a chemical nature and not of an enzymatic nature on account of the enzyme deactivation. Due to the stability of this described enzyme which drops sharply at 70° C. it is not suitable for degrading keratin as it occurs e.g. in feathers, horn or hairs on an industrial scale, that is, within a few hours to a few days since only those amounts of keratin can be added for a completely enzymatic degradation which are degraded in less than 3 h, especially clearly more rapidly than in 1 h.

DESCRIPTION OF THE INVENTION

The present invention involves the isolation of a microorganism which has proteolytic properties and can also degrade keratin in natural products in a relatively short time. Other embodiments of the present invention are are therefore a keratin-degrading enzyme composition obtainable from this microorganism and a method of degrading especially keratin.

The microorganism, strain W, was deposited with the German Collection for Microorganisms and Cell Cultures Ltd., Mascheroder Weg 1b, D-3300 Braunschweig on Mar. 12, 1992 and received the receipt number DSM 7003. Due to its properties, the microorganism received the designation *Fervidobacterium pennavorans*.

The microorganism is viable and deposited and available in accordance with the Budapest Convention on the International Recognition of the Deposition of Microorganisms for the Purpose of Patent Granting Procedures.

The microorganism as well as the proteases formed from this microorganism exhibit a sufficiently high activity, so that even an enzyme composition obtainable from the microorganism exhibits a good in-vitro activity vis-à-vis proteins, especially vis-à-vis keratin and keratin-containing substances. Thus, this enzyme composition can also be used isolated from the microorganism.

*F. pennavorans* is the first known thermophilic microorganism which utilizes feathers (e.g. chicken feathers) as substrate very well.

Not only insoluble structural proteins but also soluble proteins can be treated with the novel microorganism and also with the enzyme composition. The degradation can be complete; however, as a rule short peptide sequences which can also be further utilized industrially, if desired, are also produced in addition to individual amino acids. The biological degradation has the particular advantage over traditional methods that a chemical and/or mechanical treatment of the proteins can be eliminated. A further advantage when using the novel microorganism or the enzyme composition resides in the fact that as a consequence of the thermal stability of the enzymes the hydrolytic splitting of the peptidic bond can take place in a favorable manner at a high temperature and that on the whole the biological process becomes more secure against contamination as a result thereof so that even contamination with pathogenic microorganisms can be combatted. Since the oligopeptides and/or individual amino acids obtained during the proteolytic degradation are an excellent substrate for many microorganisms, the method in accordance with the invention is very advantageous for industrial applications. The higher temperature also yields a better substrate solubility and an easier attack of the enzyme on the substrate. Moreover, the enzyme composition of the invention is also very stable otherwise, e.g. against SDS (sodium dodecyl sulfate) and urea.

In addition to the preferred decomposition of keratin-containing substances, the novel microorganism and/or the enzyme composition can also be used to eliminate protein-containing waste, resulting in further advantages in combination with other microorganisms such as e.g. methanogenic bacteria. If the peptides or amino acids formed are further converted to methane, a savings in energy can take place at the same time. In addition, alcohols or acids can also be formed.

The enzyme composition belonging to the invention can be obtained from a culture containing the microorganism strain W, during which the culture supernatant is separated off and concentrated, if necessary. Likewise, an enzyme composition can be obtained from the maceration of cells obtained from a culture containing the microorganism strain W. It is advantageous for the obtention of the enzyme composition of the kind cited if the microorganism strain W is cultivated in a tryptone medium for enzyme production and for enzyme induction.

Another embodiment of the invention also comprises an enzyme composition which can contain one or more enzymes exhibiting protease activity and has the following characteristics:

The optimum temperature (at pH 10) is in a range of 70° to 90° C., especially approximately 80° C.;

The optimum pH (at 80° C.) is in a range of pH 7 to pH 11, especially in a range of pH 9 to pH 10;

Gel filtration exhibits a proteolytic enzyme or enzyme complex with a molecular weight of approximately 200,000 daltons and above and a determination of molecular weight with an SDS activity gel shows two bands in a range between approximately 200,000 and approximately 330,000;

The $E_{405}$ value (in comparison to blank value) after 17 hours incubation at 60° C. 0 2 mM substrate in phosphate buffer pH 7 and 0.3 mg/ml raw enzyme extract, measuring stretch 1 cm is > 0.5 for N-succinyl-Phe-pNA, N-succinyl-Ala-Ala-Pro-Phe-pNA and Z-Arg-pNA, between 0.3 and 0.5 for H-Gly-Glu-pNA, between 0.1 and 0.3 for acetyl-Ala-pNA and below 0.1 for benzoyl-DL-Arg-pNA, Z-Gly-Pro-pNA, benzoyl-Lys-pNA, Z-Arg-pNA and acetyl-Tyr-pNA;

The following inhibitors result in approximately the following residual activities at the indicated concentrations:

| Inhibitor | Residual act. (1 mM) | Residual act. (5 mM) |
|---|---|---|
| Without | 100% | 100% |
| Pefabloc SC (ser.) | 83% | — |
| PMSF (ser.) | 14% | 10% |
| EDTA (metallo.) | 93% | 85% |
| Iodoacetate (cyst.) | 83% | 76% |

The thermostabilities are as follows:

At pH 7 and 8.5 over 20 h at 70° C. and 80° C. stable,

At pH 10, 80° C. and 90° C. after 15 min total loss of activity.

At 70° C. approximately 40 % residual activity after 6 h, after 20 h total loss.

The designation "enzyme composition", which can stand for one or several enzymes, was selected since the proteolytically active extract has a very high molecular weight (approximately 200,000 in gel filtration on Superdex 200 and between approximately 200,000 and approximately 330,000 in the case of SDS-PAGE (sodium dodecylsulfate polyacrylamide gradient gel slab electrophoresis) on amido black stained gel with 0.1% gelatine as substrate). This suggests the possible existence of an enzyme complex which possibly contains the same or different subunits under the described conditions, but not separably.

In principle, the enzyme compositions of the invention as well as their method of use can be combined with enzymes or enzyme compositions—given the appropriate stability—directly, otherwise they can be combined beforehand or subsequently. This can further the degradation of oligopeptides, produced in accordance with the invention by degrading of the larger peptides, especially the insoluble peptides, to amino acids.

The microorganism strain W and/or the described enzyme compositions are used for the degradation of proteins such as in particular also keratin and of those substances containing these proteins, especially feathers, horn or hairs. The degradation of feathers is especially useful since their degradation has presented special enzymatic problems in the past on account of the particular structure of feathers and their composition.

Since more than 10,000 t/a of feather waste are produced by chicken farms and feathers consist of approximately 95 % by weight β-keratin, the invention offers an advantageous alternative to the purely chemical degradation of feathers to amino acids.

The microorganism strain W is also a source for a gene coding a keratinase which can be inserted into other microorganisms. This is done employing conventional methodologies such as those in to Winnaker, E. L., *Gene und Klone: Eine Einführung in die Gentechnologie VCH, Weinheim*, 1985; Maniatis, Fritsch, Sambrock: *Molecular Cloning, A Laboratory Manual*, Cold Spring Harbor Lab., New York, 1989. The gene from the microorganism strain W coding a keratinase is inserted into an *E. coli* or Bacillus and the *E. coli* or Bacillus is then grown in order to obtain the keratinase. The keratinase can then be readily separated from this *E. coli* or Bacillus by heating on the basis of its temperature stability. Since the microorganism strain W can only be grown slowly as an anaerobic microorganism the insertion in accordance with the invention into the easy-to-grow *E. coli* or Bacillus permits a more rapid cultivation and higher enzyme yields.

A method belonging to the invention for the hydrolysis of peptides, especially of keratin or keratin-containing substances such as feathers, hairs or horn into oligopeptides and/or amino acids at a temperature > 50° C. by means of one or more enzymes is carried out in such a manner that the hydrolysis takes place at a temperature between 50° C. and 105° C., the pH is adjusted between 4 and < 11 and that care is taken by means of the selection of the added amount of enzyme, but especially by means of the selection of the temperature and of the pH that the enzymatic degradation is a multiple of any potentially accompanying chemical degradation. A pH of at the most 10.5 is especially advantageous thereby. The higher the pH is, the higher the proportion of the chemical degradation, at the same time as which the amount of racemized amino acids or of oligopeptides with racemized amino acids also increases.

Moreover, according to the present invention a method for the hydrolysis of peptides, especially keratin or keratin-containing substances such as feathers, hairs or horn into oligopeptides and/or amino acids can be carried out by means of one or more enzymes at a temperature $\geq 70°$ C. in which the enzymatic degradation is anaerobic. A transfer of the anaerobic degradation into the first-described method is especially advantageous. The anaerobic method can basically be carried out at a pH between 4 and 12 and again the pH below 11 and especially up to 10.5 is preferred. Especially clean amino acids can be obtained with the anaerobic degradation; in particular, sulfur-containing amino acids such as cystine and cysteine are not oxidized.

A third variation of the method involves the degradation of peptides, especially keratin or keratin-containing substances such as feathers, hairs or horn are hydrolyzed into oligopeptides and/or amino acids using one or more enzymes and a mesophilic microorganism which is accessible as described above and which contains a gene which codes a protease active at $\geq 70°$ C. especially keratinase, which mesophilic microorganism is reacted at $\geq 70°$ C. in aqueous medium with the protein, especially keratin or keratin-containing substance, or which mesophilic microorganism containing the described gene is heated in aqueous medium to $\geq 70°$ C. and the aqueous medium, optionally after separation of precipitated components such as, e.g., parts of the mesophilic microorganism, is compounded with the protein, especially keratin or with the keratin-containing substance. The gene coding the protease, especially keratinase, is especially a gene, as described above, inserted into the mesophilic microorganism. This method is especially suitable for industrial peptide hydrolysis, especially of feathers. The method permits a practically contamination-free operation in which the amino acid and/or oligopeptide products accumulate relatively cleanly and/or can be separated from any impurities such as, e.g., parts of the microorganism in a simple manner, e.g., by filtration.

According to the present invention a further method for the hydrolysis of especially insoluble proteins such as keratin or keratin-containing substances such as feathers, hairs or horn into oligopeptides and/or amino acids at a temperature > 50° C. and by means of one or more enzymes is advantageous in which the hydrolysis is carried out with such an amount of enzyme, at such a pH and such a temperature that an added, insoluble substrate, especially feathers, hairs or horn, is dissolved at the earliest after 3 hours and it is especially advantageous if at least 50 % by weight of this substrate is dissolved after 24 h. This method is terminated with advantage after 1 to 4 days, at which time especially at least 80 % by weight, preferably over 90 % by weight and especially advantageously practically the entire substrate is dissolved.

If keratin or keratin-containing substance, especially feathers, are used in the methods cited above, a pretreatment such as e.g. an autoclaving, especially a treatment at a temperature $\geq 130°$ C. can be eliminated with advantage and it is especially advantageous to even eliminate a pretreatment $\geq 120°$ C. Such pretreatments were customary in the prior art dealing with the hydrolysis of feathers; however, racemization of the amino acids occurs.

According to the invention the above-mentioned methods can also be carried out in two stages, that is, after dissolving at least a part of the substrate used, especially after dissolving more than 50 % by weight of the substrate used, the hydrolysate is further treated with one or more other peptidases, optionally under other conditions (temperature, pH). This serves for a more rapid or a more extensive hydrolysis of oligopeptides produced.

The invention also comprises a method for the enzymatic hydrolysis of proteins, especially of keratin and of such substances containing these proteins, especially feathers, horn or hairs, which hydrolysis is carried out with one of the enzyme compositions described above and/or with the microorganism strain W. The enzyme compositions described above can basically be used in all methods in accordance with the invention.

SHORT DESCRIPTION OF THE DRAWINGS

The invention is described in detail in the following using examples and figures.

DETAILED DESCRIPTION FOR CARRYING OUT THE INVENTION

Strain Characterization

Figure 1:
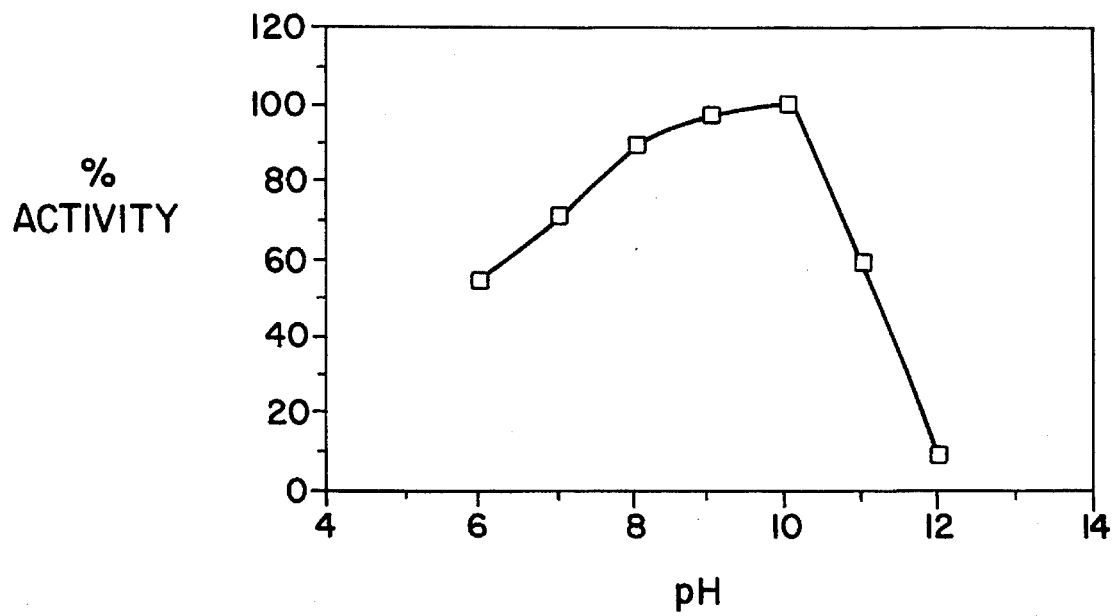
FIG. 1 shows the optimum pH of an enzyme composition in accordance with the invention.

The novel microorganism strain W was isolated from a hot spring in the Azores. It can be cultivated under nitrogen at 70° C. Hungate tubes [capillary t.] can be used for this which are filled with a medium of the following composition:

| | |
|---|---|
| $K_2HPO_4$ | 1.6 g |
| $NaH_2PO_4$ | 1.0 g |
| $(NH_4)_2SO_4$ | 1.5 g |
| NaCl | 3.0 g |
| $CaCl_2 \times 2\ H_2O$ | 0.1 g |
| $MgSO_4 \times 7\ H_2O$ | 0.3 g |
| $FeCl_2 \times 6\ H_2O$ | 6.0 mg |
| Trypton | 1.0 g |
| Yeast extract | 1.0 g |
| Trace elements | 1.0 ml |
| Vitamins | 1.0 ml |
| Resazurin (1 mg/ml) | 1.0 ml |
| $NaHCO_3$ | 1.0 g |
| Cysteine HCl | 0.5 g |
| Aqua dest ad | 1.0 l |
| pH (with 6 N HCl) | 6.0 (after the autoclaving approximately 6.3) |
| Trace elements: | |
| $MnCl_2 \times 4\ H_2O$ | 1.0 g |
| $CoCl_2 \times 6\ H_2O$ | 1.0 g |
| $NiCl_2 \times 6\ H_2O$ | 0.5 g |
| $ZnCl_2$ | 0.5 g |
| $CuSO_4$ | 0.5 g |
| $H_3BO_4$ | 0.2 g |
| $Na_2MoO_4 \times 2\ H_2O$ | 0.1 g |
| $Na_2SeO_3 \times 5\ H_2O$ | 0.1 g |
| $VOSO_4 \times 5\ H_2O$ | 0.03 g |
| aqua dest ad | 1.0 l |
| Vitamin solution | |
| Biotin | 0.2 g |
| Folic acid | 0.2 g |
| Pyridoxine/HCl | 1.0 g |
| Thiamine/HCl | 0.5 g |
| Riboflavin | 0.5 g |
| Nicotinic acid | 0.5 g |
| DL-calcium pantothenate | 0.5 g |
| Vitamin $B_{12}$ | 0.01 g |
| p-amino benzoate | 0.5 g |
| Lipoic acid | 0.5 g |
| Aqua dest ad | 1.0 l |
| pH with 1 N NaOH | 7.0 |

Either 0.2 % trypton or insoluble protein, e.g. in the form of a feather is added to the medium as substrate. The Hungate tubes are subsequently gassed with nitrogen. A sterilization then takes place under generally customary conditions such as e.g. at 120° C. for 30 min. However, if skeletal [fibrous] proteins are used the mixture is sterilized at lower temperatures, e.g. at 100° C. for 60 min in order that the natural proteins do not denature. The following incubation can take place at high temperatures, especially at 70° C. Under anaerobic conditions the cells grow in approximately 8 to 12 h and a degradation of the skeletal proteins can be determined after 3 days.

A sporogenesis was not able to be demonstrated upon cultivation on spore medium with and without glucose. No catalase could be demonstrated via a peroxidase test.

In addition, the novel microorganism strain W exhibits the following degradation properties:

| Substrate | Degradation |
|---|---|
| Lactose | − |
| Glucose | − |
| Fructose | −* |
| Maltose | + |
| Xylose | + |
| Amylase | + |
| Arabinose | − |
| Inulin | − |
| Tween 80 | − |
| HEC (cellulose) | − |
| Pullulan | + |

-continued

| Substrate | Degradation |
| --- | --- |
| Glycogen | + |
| Starch | + |
| Gelatine | − |
| Peptone | −* |
| Bactopeptone | −* |
| Collagen | − |
| Casein | − |
| Trypton | + |
| Amylopectin | − |
| Succinate | − |
| Yeast extract | + |
| Gram property | Gram-negative* |
| KOH test | no reaction |
| Xylanaleban[e?] | − |

*not unequivocal

A determination of the guanosine + cytosine content of the DNA by means of HPLC yielded on the average G + C=40.0 ± 0.6 mole % (three determinations). The determination took place analogously as described in Anal. Biochem. 81, (1977), 461–6 for the DNA isolation; Int. J. Syst. Bact. 39, (1989), 159–167 for the DNA degradation, reference DNA as well as G + C determination and FEMS Microbiology Letters 25, (1984), 125–8 for the chromatographic conditions.

Analytic column NUCLEOSIL 100–5C18 (250×4 mm) with precolumn NUCLEOSIL 100–5C18 (20×4 mm); temperature 26° C., mobile solvent 0.6 M $(NH_4)H_2PO_4$ acetonitrile 80:6 (v/v), pH 4.4, 0.7 ml/min, pressure approximately 120 bar, calibration with non-methylated LAMBDA-DNA (sigma), G + C content 49.858 mole DNA degradation with P1 nuclease and dephosphoxylation with alkaline phosphate from calf serum (bovine alkaline phosphate).

Production of a Raw Extract

Cells of a fermenter culture are macerated (approximately 1 g/20 ml Na-phosphate 50 mM pH 6.8 buffer) by ultrasound. (15 min, 50 %, stage (setting) 6–7, average sonication peak, Branson Sonifier). After microscopic control of successful maceration the raw extract is centrifuged for 20 min, 4° C., 35,000 xg. The supernatant obtained in this manner is used for the enzyme tests.

Activity: approximately 0.3–0.8 U/ml, according to maceration

Protein: approximately 1–2 mg/ml

Determination of the proteolytic activity

Determination of the proteolytic activity vis-à-vis soluble proteins

The principle of measuring proteolytic activity vis-à-vis soluble proteins is based on the fact that aromatic amino acids are released by means of enzymatic activity from proteins such as e.g. casein or bovine serum albumin. These acids can be photometrically detected after stopping off the reaction and precipitation of the non-split protein with trichloroacetic acid in the supernatant at 280 nm.

Reaction Batch 0.45 ml 0.25 % (w/v) casein solution (Hammersten Quality) in an appropriate B & R buffer (Britton & Robinson, J. Chem. Soc. (1931), p. 1456. A solution containing 0.4 M $H_3PO_4$, 0.4M $CH_3COOH$ and 0.4M $H_3BO_3$ in water is adjusted to the desired pH with 0.2 N NaOH) is pipetted on ice with 0.05 ml enzyme-containing specimen into E-Cups and incubated, depending on the activity, up to 60 min at the optimal temperature for the enzyme (80° C.) and the optimal pH (10). The batch is then compounded for stopping off and precipitating the proteins with 0.5 ml 10 % (w/v) trichloroacetic acid (TCA), incubated for 15–30 min at room temperature and then centrifuged for 10 min at 13000 rpms in an Eppendorf centrifuge (Heraeus Sepatech, Osterode). The extinction of the clear supernatant is measured at 280 nm in a quartz cuvette against a non-incubated blank reading.

In order to determine the enzyme activity, a tyrosine calibration curve is recorded in the range of 0–1 μM/batch. An enzyme activity (1 unit) is defined as that amount which released 1 μmole aromatic amino acids/min. The following computation results from the rise of the calibration curve:

$$U/l = \frac{A \times 1 \times 20{,}000}{t \,(\text{min})}$$

Production of the enzyme composition

In order to obtain the enzyme composition of the invention the cells cultivated in a pure culture or mixed culture are separated at 10,000 × g so that the enzyme composition is located in the supernatant. From here a concentration can be performed e.g. by means of cross-flow filtration or via Amicon chambers.

However, it turned out that a part of the enzymes located in the enzyme composition is membrane-bound, so that in order to obtain the enzymes the cells are advantageously macerated. This maceration can take place e.g. by ultrasound or by a French press. Subsequently, a further concentration of the enzymes can be carried out, as described above.

Characterization of the Enzyme Composition

The enzyme composition of the invention can consist of one enzyme or of several enzymes. If this composition is obtained from a mixed culture containing the novel microorganism, external enzymes of other microorganisms can also be contained.

Figure 2:
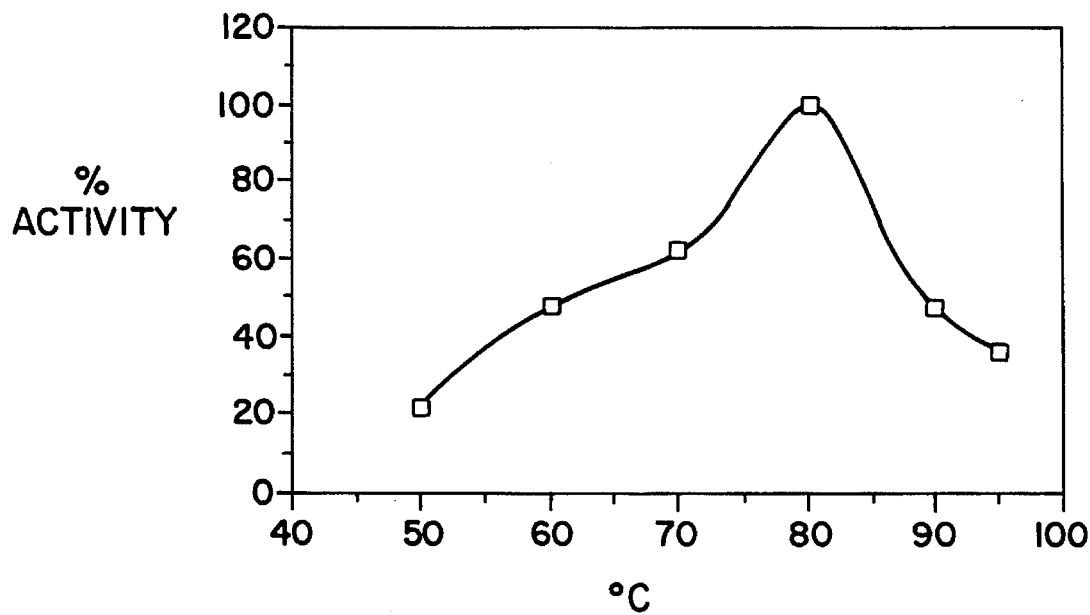
FIG. 2 shows the optimum temperature of the enzyme composition of FIG. 1.

The protease activity of the enzyme composition was determined in several tests (Klingeberg, M., Haswa, F., Antranikian, G., (1990), "Properties of Extremely Thermostable Protease from Anaerobic Hyperthermophilic Bacteria," Appl. Microbiol. Biotechnol. 43:715–719). 0.25 % substrate solutions (casein in B & R buffer of the desired pH) were used thereby and the activity determined as indicated above. FIG. 1 shows the optimum pH at 80° C. The latter is in a range of pH 4 to pH 12, preferably in a range of pH 7 to pH 11 and especially in a range of pH 9 to pH 10. The optimum temperature according to FIG. 2 was determined at pH 10. An enzyme activity is recognized in the broad range from 50° to 105° C., preferably in the range of 70° to 90° C. and especially at 80° C. In order to determine the thermostability specimens are taken after 15 min., 30 min., 1 h, hourly up to 6 h and after 20 h and the activity determined. Stable means that no appreciable (> 10 %) activity loss occurs between 6 h and 20 h.

The Influence of Various Inhibitors on the Protease Activity

The inhibiting action of various inhibitors on the protease activity furnishes information about the active center and the reaction mechanism of the enzymes. Phenylmethylsulfonyl fluoride (PMSF) and diisopropylfluorophosphate (DFP) bond to the OH group of the serine in the active center of serine proteases and inhibit the latter irreversibly. Ethylene diamine tetraacetate $Na_2$ salt (EDTA) is a metal chelating agent and inhibits metalloproteases. Proteases in which cysteine is present in the active center can be irreversibly inhibited by iodoacetate. In order to determine the active center of the thermostable proteases they are incubated together with appropriate inhibitors at room temperature and pH 7.0 in order to avoid a hydrolysis of DFP and PMSF.

Reaction Batch

470 μl 0.25 % (w/v) casein in 50 M, pH 10—buffer (B & R)

25 μl enzyme solution

5 μl inhibitor stock [strain]solution (see below)

When using 5 μl inhibitor stock solution the final concentration corresponds to 1 mM. When using 25 μl inhibitor solution (final concentration 5 mM), only 450 μl substrate solution are accordingly used. The batches are at first incubated without substrate at room temperature (1 h) and then with substrate for 1 h at the temperature which is optimum for the enzyme.

After the incubation the reaction is stopped with 500 μl of a 10 % (w/v) solution of trichloroacetic acid and the remaining activity determined as described above. The following inhibitor solutions are used:

PMSF 17.3 % (w/v) in ethanol

EDTA 3.56 % (w/v) in $H_2O$ bidistillate

Iodoacetate 14.4 % (w.v) in $H_2O$ bidistillate

The hydrolysis of chromogenic peptide substrates by proteases of the culture supernatant ($E_{405}$ value)

In order to determine the substrate specificity of the proteases the cited chromogenic peptide substrates are incubated in a final concentration of 0.2 mM together with cell-free raw extract.

The incubation takes place below the temperature optimum and pH optimum of the proteases in order to avoid a thermal and pH-dependent, non-enzymatic hydrolysis of the peptide substrates.

Reaction Batch

900 μl 0.2 mM (w/v) substrate solution in 50 mM Na-P-buffer, pH 7.0

100 μl enzyme specimen incubation for 17 h at 60° C.

The released p-nitroaniline is subsequently measured immediately against a non-incubated blank reading at an extinction of 405 nm.

SDS Gel Electrophoresis

The SDS gel has a layer thickness of 1.5 mm. The concentration of the collecting gel is 4.5 % (w/v), that of the separating gel 11.5 % (w/v). The following solutions are used to produce the gels:

| Acrylamide solution: | |
| --- | --- |
| Acrylamide | 29.2 g |
| N,N-methylene bis acrylamide | 0.8 g |
| Distilled $H_2O$ ad | 100 ml |

This solution is filtered in order to remove undissolved particles.

| Separating-gel buffer: | |
| --- | --- |
| Tris (α,α,α-tris(hydroxymethyl)) methylamine) | 18.15 g |
| SDS | 0.40 g |
| Distilled $H_2O$ ad | 100 ml |

Before the addition of SDS the pH is adjusted with concentrated HCl to 8.9.

| Collecting buffer: | |
| --- | --- |
| Tris | 6.05 g |
| SDS | 0.40 g |
| Distilled $H_2O$ ad | 100 ml |

Before the addition of SDS the pH is adjusted with concentrated HCl to 6.8.

| Ammonium persulfate solution: | |
| --- | --- |
| Ammonium persulfate | 0.10 g |
| Distilled $H_2O$ | 0.94 g |
| Electrophoresis buffer: | |
| Tris | 3.00 g |
| Glycine | 14.40 g |
| SDS | 1.00 g |
| Distilled $H_2O$ ad | 1000 ml |

The ammonium persulfate solution is either freshly prepared before use or stored in portions in Eppendorf reaction containers at −20° C. and not thawed until shortly before use. Whereas the electrophoresis buffer is always prepared fresh, all other solutions can be stored for several weeks at 4° C.

Production of the Gels

In order to produce the plate gels the separating gel is poured first. To this end

| Separating-gel buffer | 1.4 ml |
| --- | --- |
| Acrylamide solution | 2.1 ml |
| Distilled $H_2O$ | 2.6 ml | are mixed well and degassed with the aid of a water pump. The polymerization is started by the addition of

| Ammonium persulfate solution | 20 μl |
| --- | --- |
| TEMED | 6 μl | and the solution filled into the chamber until 1.5 cm space for the collecting gel remains. The coating over of the gel with 1 ml distilled $H_2O$ prevents drying out. After approximately 60 min the polymerization process is concluded and the collecting gel can be poured. To this end

| Collecting-gel buffer | 0.70 ml |
| --- | --- |
| Acrylamide solution | 0.26 ml |
| Distilled $H_2O$ | 1.04 ml | are mixed, degassed and the polymerization started by the addition of

| | |
|---|---|
| Ammonium persulfate solution | 10 µl |
| TEMED (N,N,N',N'-tetramethylethylene diamine) | 2 µl. |

Before the collecting gel is poured the water is first decanted from the separating gel. A comb set free of air bubbles into the still liquid gel serves to form pockets.

Preparation of the Specimens

Up to 50 µl protein solution with up to 50 µg protein are compounded with 10 µl denaturing buffer containing the following components:

| | | |
|---|---|---|
| SDS | | 2.00 g |
| 2-mercaptoethanol | | 3.00 g |
| 10 mM NaP buffer, pH 7.0 ad | | 100 ml |

The batch is incubated 5 min at 100° C., then compounded with 2 µl bromophenol blue solution as well as a spatula tip of saccharose and applied onto the gel with a Hamilton syringe.

Carrying out of the Electrophoresis

At first, a constant current strength of 10 mA/1.5 mm gel thickness and 10 cm gel width is applied for the inmigration of the specimens. After the specimens have migrated into the collecting gel the current strength is raised to 20 mA.

Silver Coloring

During the separation of very slight amounts of protein by gel electrophoresis the detection of the protein bands takes place by staining with silver. For this, the gel is incubated after the electrophoresis in the solutions cited below on a shaker

| | |
|---|---|
| Fixer | 60 min |
| 50% (v/v) EtOH | 3 × 20 min |
| 0.30% (w/v) Na$_2$S$_2$O$_5$ | 1 min |
| Distilled H$_2$O (changed 3 ×) | 1 min |
| Silver solution | 20 min | and rinsed [washed] twice with distilled H$_2$O. Then, the gel is incubated under gentle swirling in developer solution until the protein bands become clearly visible. The coloring reaction is stopped by placing the gel into a 50 mM solution of EDTA. The gel can be stored several weeks in the last-named solution.

| | | |
|---|---|---|
| Fixer: | Ethanol | 30 ml |
| | Acetic acid | 10 ml |
| | Formaldehyde solution (37%) | 50 µl |
| | Distilled H$_2$O ad | 100 ml |
| Silver solution | AgNO$_3$ | 0.1 g |
| | Formaldehyde solution (37%) | 75 µl |
| | Distilled H$_2$O ad | 100 ml |
| Developer: | Na$_2$CO$_3$ | 6 g |
| | Na$_2$S$_2$O$_5$ | 0.4 mg |
| | Formaldehyde solution (37%) | 50 µl |
| | Distilled H$_2$O ad | 100 ml. |

Demonstration of proteolytic activity in the SDS polyacrylamide gel.

Enzymes with proteolytic activity can be indirectly demonstrated via the coloring of gelatine which is poured into the gel. Tor this, an 11% SDS separating gel is poured as described above. However, as a deviation instead of 2.6 ml H$_2$O only 2.0 ml is added and the remaining 0.6 ml is replaced by 1% gelatine in 100 mM glycine buffer, pH 8.5. This results in a final concentration of 0.1% gelatine in the gel. The collecting gel is poured without gelatine, as described above. The preparation of the specimens and the carrying out of the electrophoresis takes place as above. The electrophoresis is followed by a 60 minute incubation of the gel in a 2.5 % triton X-100 solution at 4° C. in order to dissolve SDS out of the gel. The gel is then incubated according to the activity applied for 5–30 min in a 50 mM buffer under optimum conditions (pH 10, 80° C.) and subsequently fixed and colored for 60 min in coloring solution. Bands with proteolytic activity become visible after approximately 3 hours decoloration as bright bands in the gel colored blue.

| | | |
|---|---|---|
| Coloring solution: | Amido black | 0.1 g |
| | Ethanol | 30 ml |
| | Glacial acetic acid | 10 ml |
| | Distilled H$_2$O ad | 100 ml |
| Decolorant: | Ethanol | 30 ml |
| | glacial acetic acid | 10 ml |
| | Distilled H$_2$O ad | 100 ml. |

Gel filtration on Superdex 200 (HPLC)

Enzyme Raw Extract 1 mg/ml protein 0.6 U/ml

Column

Superdex high-load 200 16/60 (120 ml)

Buffer

NaP pH 6.8

Flow Rate 0.5 ml/min

Active Protein Peak

In the excluded volume, is therefore (greatest calibrating protein: 200,000) greater than 200,000

| The influence of metal ions on the proteolytic activity | | |
|---|---|---|
| Metal ion | ca. % activity 1 mM | ca. % activity 5 mM |
| AgCl$_2$ | 0 | 0 |
| CaCl$_2$ | 85 | 117 |
| CoCl$_2$ | 143 | 187 |
| CuCl$_2$ | 17 | 0 |
| FeCl$_2$ | 127 | 0 |
| FeCl$_3$ | 93 | 0 |
| MgCl$_2$ | 171 | 125 |
| MnCl$_2$ | 110 | 120 |
| NaCl | 86 | 116 |
| NcMoO$_4$ | 91 | 95 |
| NaSe$_2$O$_3$ | 96 | 136 |
| NaWO$_4$ | 75 | 134 |
| NiCl$_2$ | 72 | 44 |
| VOSO$_4$ | 87 | 44 |
| ZnCl$_2$ | 57 | 37 |

The metal ions are dissolved in a buffer, 50 mM Na—P; pH 6.8. 50 µl of this solution are incubated with 50 µl raw extract for 1 h at room temperature, then 400 µl substrate (0.25 %, pH 10) are added and incubated for 1 h at 80° C. TCA precipitation and determination of activity are carried out as described above.

Figure 3:
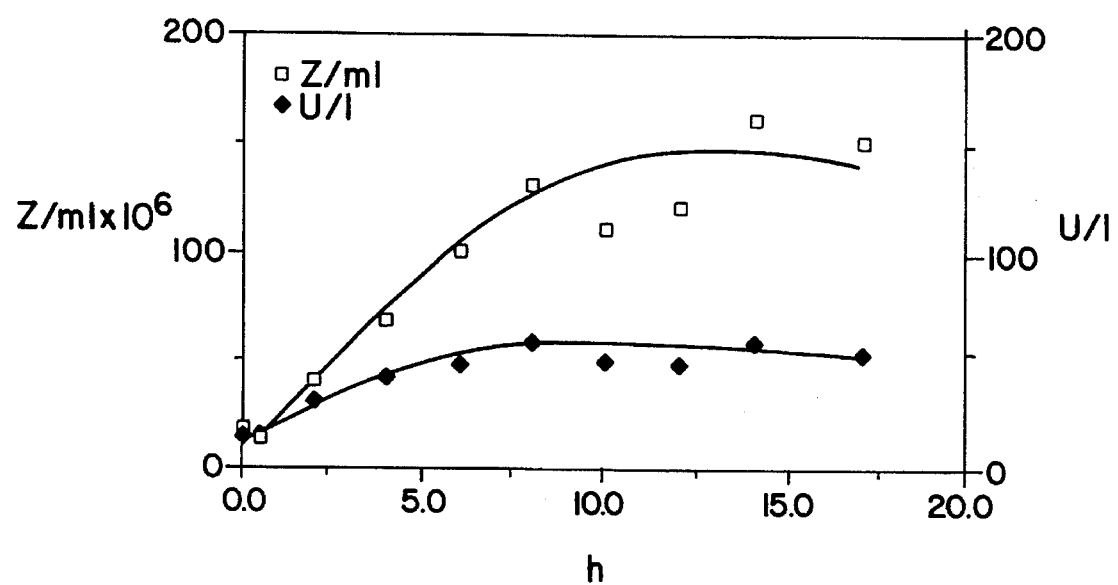
FIG. 3 shows the enzyme activity of this enzyme composition.
Figure 4:
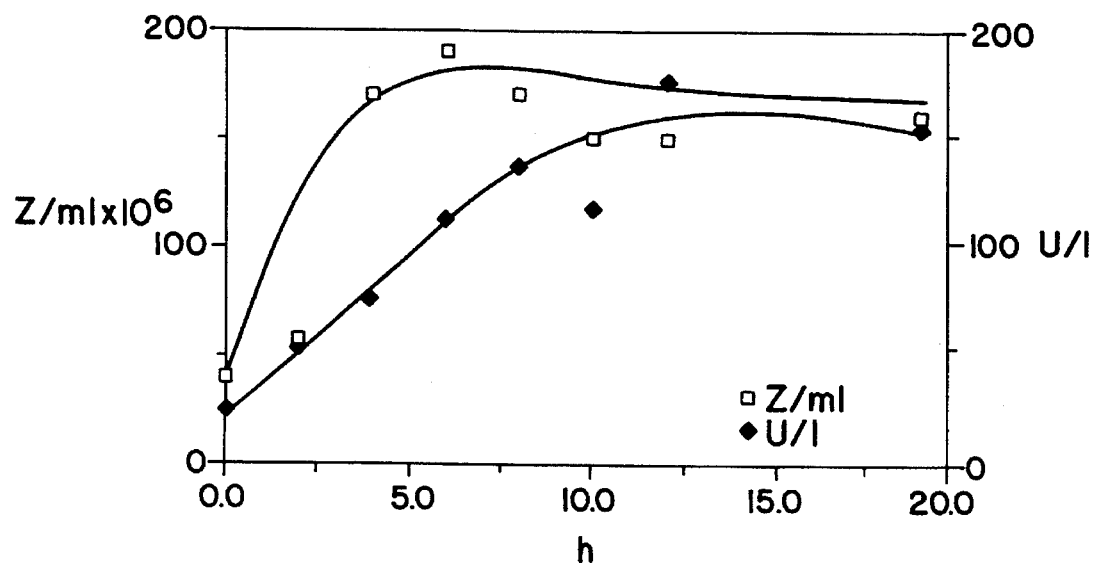
FIG. 4 shows the enzyme activity analogously to FIG. 3 with the addition of trypton.

In a further test the growth of the novel microorganism on complex medium with 0.25 % feathers as substrate was investigated and at the same time the enzyme activity determined (FIG. 3). If 0.25 % trypton is added to the complex medium (FIG. 4) the enzyme activity clearly rises.

Figure 5:
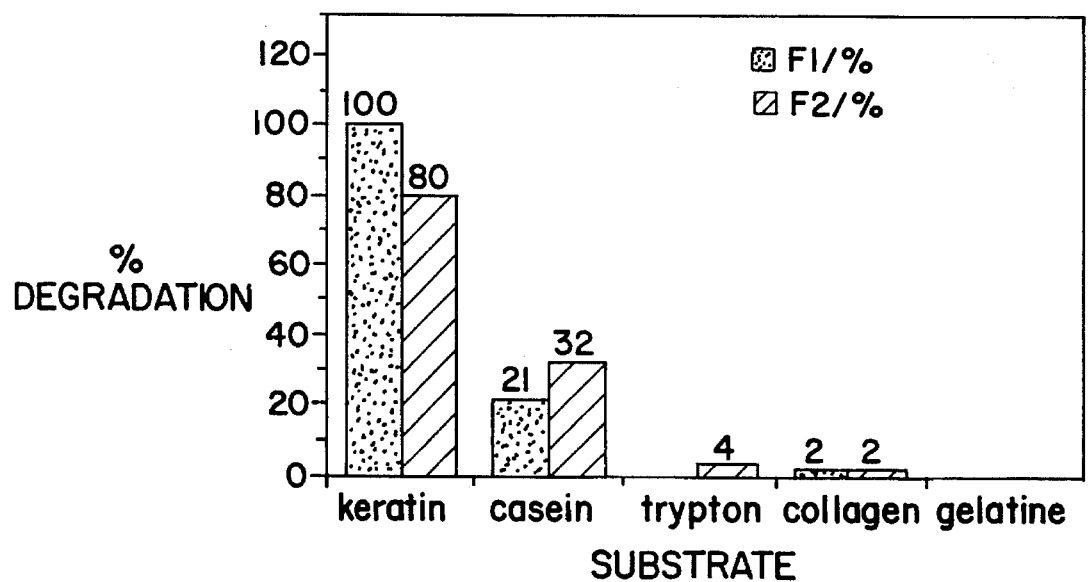
FIG. 5 shows the enzymatic degradation of soluble substrates.
Figure 6:
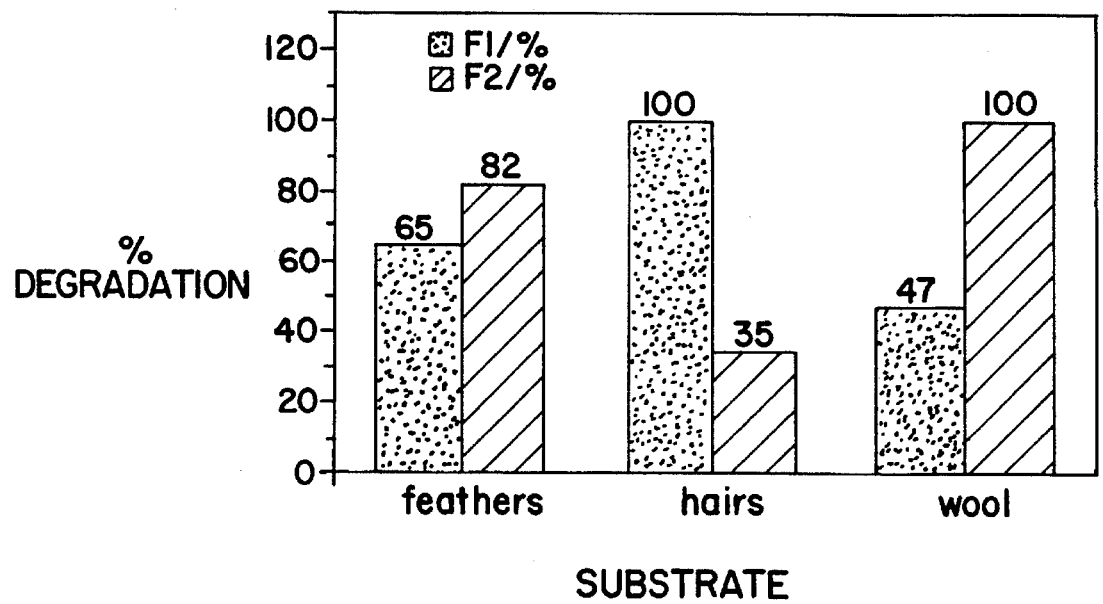
FIG. 6 shows the enzymatic degradation of isoluble substrates.
Figure 7A:
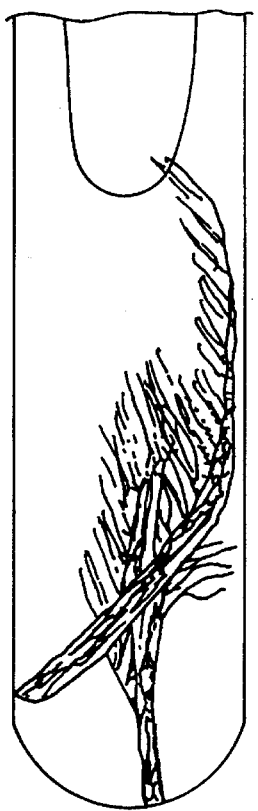
FIG. 7 shows the degradation of feathers within 2 days.
Figure 7B:
Figure 7C:
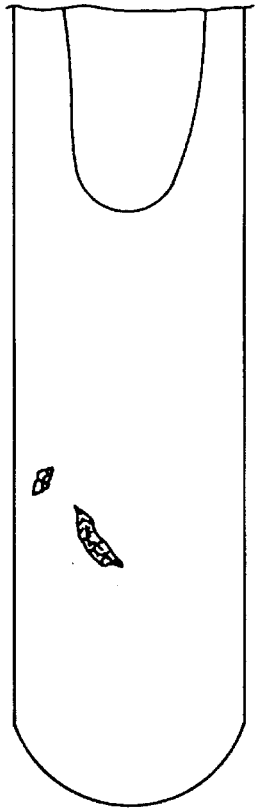

Finally, FIGS. 5 and 6 show the degradation of soluble and of insoluble substrates. After the addition of a defined amount of enzyme (0.1 U/ml) the substrate degradation in terms of percent was determined, during which cells of the novel microorganism grown on feather substrate (left beam, F 1) were compared with cells grown on tryptone (right beam, F 2).

In all, an enzymatic protein degradation can be carried out with entire cells of the novel microorganism strain W or in vitro in the presence of an enzyme composition in accordance with the invention. The in vitro treatment also has the possibility that a proteolysis can also be carried out under anaerobic conditions at 50° to 100° C. and e.g. at pH 10, which anaerobic variant (see above) is preferred.

What is claimed is:

1. An isolated keratinase which has a molecular weight of approximately 200,000 daltons as measured-by gel filtration and which is isolated from *Fervidobacterium pennavorans* DSM 7003 and has an optimal temperature range between 70° and 90° C. at a pH of 10 and an optimal pH range between 7 and 11 at 80° C.

2. An isolated enzyme composition which contains keratinase and is obtainable from *Fervidobacterium pennavorans* DSM 7003 and which keratinase has the following characteristics:

capable of degrading keratin;

optimum temperature at a pH 10 is in a range of 70° to 90° C.;

optimum pH at 80° C. is in a range of pH 7 to pH 11;

gel filtration exhibits a molecular weight of approximately 200,000 daltons and a determination of molecular weight with an SDS activity gel shows two bands in a range between approximately 200,000 and approximately 330,000;

$E_{405}$ value, in comparison to a blank value, after 17 h incubation at 60° C., 0.2 mM substrate in phosphate buffer pH 7 and 0.3 mg/ml raw enzyme extract, measuring stretch 1 cm is > 0.5 for N-succinyl-Phe-pNA, N-succinyl-Ala-Ala-Pro-Phe-pNA and Z-Arg-pNA, between 0.3 and 0.5 for H-Gly-Glu-pNA, between 0.1 and 0.3 for acetyl-Ala-pNA and below 0.1 for benzoyl-DL-Arg-pNA, Z-Gly-Pro-pNA, benzoyl-Lys-pNA, Z-Arg-pNA and acetyl-Tyr-pNA;

inhibitors result in approximately the following residual activities at the indicated following concentrations:

| Inhibitor | Resiudual act. (1 mM) | Residual act. (5 mM) |
|---|---|---|
| Without | 100% | 100% |
| Pefabloc SC (ser.) | 83% | — |
| PMSF (ser.) | 14% | 10% |
| EDTA (metallo.) | 93% | 85% |
| Iodoacetate (cyst.) | 83% | 76%; |

The thermostabilities are as follows:

at pH 7 and 8.5 is stable over 20 h at 70° C. and 80° C., at pH 10, 80° C. and 90° C. after 15 min total loss of activity, and at 70° C. approximately 40% residual activity after 6h, and after 20 h total loss.

3. The isolated enzyme composition according to claim 2 wherein culturing *Fervidobacterium pennavorans* DSM 7003 in a tryptone medium induces production of the Keratinase.

4. The isolated enzyme composition according to claim 2 wherein the keratinase has an optimum temperature of approximately 80° C. at a pH of 10.

5. The isolated enzyme composition according to claim 2 wherein the keratinase has an optimum temperature at 80° C. at a pH between 9 and 10.

* * * * *